US 8,501,466 B2

(12) United States Patent
Nair et al.

(10) Patent No.: US 8,501,466 B2
(45) Date of Patent: Aug. 6, 2013

(54) VECTOR

(75) Inventors: Venugopal Nair, Woking (GB); Luke Lambeth, Woking (GB)

(73) Assignee: The Pirbright Institute, Pirbright (GB)

( * ) Notice: Subject to any disclaimer, the term of this patent is extended or adjusted under 35 U.S.C. 154(b) by 0 days.

(21) Appl. No.: 12/997,844

(22) PCT Filed: Jun. 11, 2009

(86) PCT No.: PCT/GB2009/001471
§ 371 (c)(1),
(2), (4) Date: Mar. 11, 2011

(87) PCT Pub. No.: WO2009/150431
PCT Pub. Date: Dec. 17, 2009

(65) Prior Publication Data
US 2012/0076823 A1 Mar. 29, 2012

(30) Foreign Application Priority Data
Jun. 13, 2008 (GB) .................................. 0810912.6

(51) Int. Cl.
*C12N 15/63* (2006.01)
*C07H 21/02* (2006.01)
*C07H 21/04* (2006.01)

(52) U.S. Cl.
USPC ................... 435/320.1; 536/23.1; 536/24.5

(58) Field of Classification Search
None
See application file for complete search history.

(56) References Cited

U.S. PATENT DOCUMENTS

| 4,040,388 | A | 8/1977 | Miller |
| 4,469,047 | A | 9/1984 | Miller |
| 4,593,646 | A | 6/1986 | Miller et al. |
| 4,681,063 | A | 7/1987 | Hebrank |
| 2005/0112678 | A1* | 5/2005 | Yang .................................. 435/6 |

OTHER PUBLICATIONS

Chen et al. (Virology 365, 2007, 464-472).*
Yao et al. (Journal of Virology, Apr. 2008, vol. 82, No. 8, pp. 4007-4015).*
Carmona et al. (Molecular Therapy, vol. 13, No. 3, Feb. 2006, pp. 411-421).*
Shin et al. (PNAS, Sep. 12, 2006, vol. 103, No. 37, pp. 13759-13764).*
Aagaard et al., RNAi therapeutics: principles, prospects and challenges. *Adv. Drug Deliv. Rev.* 59(2-3):75-86 (2007).
Bhuyan et al., Short interfering RNA-mediated inhibition of herpes simplex virus type 1 gene expression and function during infection of human keratinocytes. *J. Virol.* 78(19):10276-81 (2004).
Brummelkamp et al., A system for stable expression of short interfering RNAs in mammalian cells. *Science*, 296(5567):550-3 (2002).
Chang et al., Inhibition of the Epstein-Barr virus lytic cycle by Zta-targeted RNA interference. *J. Gen. Virol.* 85(6):1371-9 (2004).
Chen et al., Inhibition of Merek's disease virus replication by retroviral vector-based RNA interference. *Virology*, 377(2): 265-72 (2008).
Chen et al., RNA interference targeting VP1 inhibits foot-and-mouth disease virus replication in BHK-21 cells and suckling mice. *J. Virol.* 78(13):6900-7 (2004).
Coburn et al., Potent and specific inhibition of human immunodeficiency virus type 1 replication by RNA interference. *J. Virol.* 76(18):9225-31 (2002).
Cullen, Viruses and microRNAs. *Nat. Genet.* 38(Suppl):S25-30 (2006).
de Fougerolles et al., Interfering with disease: a progress report on siRNA-based therapeutics. *Nat. Rev. Drug Discov.* 6(6):443-53 (2007).
Domitrovich et al., Multiple, dispersed human U6 small nuclear RNA genes with varied transcriptional efficiencies. *Nucl. Acids Res.* 31(9):2344-52 (2003).
Elbashir et al., Duplexes of 21-nucleotide RNAs mediate RNA interference in cultured mammalian cells. *Nature*, 411:494-8 (2001).
Ge et al., RNA interference of influenza virus production by directly targeting mRNA for degradation and indirectly inhibiting all viral RNA transcription. *Proc. Natl. Acad. Sci. USA*, 100(5):2718-23 (2003).
Godfrey et al., Inhibiting primary effusion lymphoma by lentiviral vectors encoding short hairpin RNA. *Blood*,105(6):2510-8 (2005).
Griffiths-Jones et al., miRBase: tools for microRNA genomics. *Nucl. Acids Res.* 36:D154-8 (2008).
Hannon et al., RNA interface. *Nature*, 418: 244-51 (2002).
Hong et al., Herpes simplex virus RNAi and neprilysin gene transfer vectors reduce acculation of Alzheimer's disease-related amyloid-beta peptide in vivo. *Gene Ther.* 13(14): 1068-79 (2006).
Jia et al., Inhibition of gammaherpesvirus replication by RNA interference. *J. Virol.* 77(5):3301-6 (2003).
Kudo et al., Usage of putative chicken U6 promoters for vector-based RNA interference. *J. Reprod. Dev.* 51(3):411-7 (2005).
Lagos-Quintana et al., Identification of tissue-specific microRNAs from mouse. *Curr. Biol.* 12(9):735-9 (2002).
Lambeth et al., Comparison of bovine RNA polymerase III promoters for short hairpin RNA expression. *Anim. Genet.* 37(4):369-72 (2006).
Lambeth et al., Targeting Marek's disease virus by RNA interference delivered from a herpesvirus vaccine. *Vaccine*, 27(2): 298-306 (2009).
Liu et al., Cross-inhibition to heterologous foot-and-mouth disease virus infection induced by RNA interference targeting the conserved regions of viral genome. *Virology*, 336(1):51-9 (2005).
Mallanna et al., Inhibition of Anatid Herpes Virus-1 replication by small interfering RNAs in cell culture system. *Virus Res.* 115(2):192-7 (2006).
Murphy et al., Suppression of immediate-early viral gene expression by herpesvirus-coded microRNAs: Implications for latency. *Proc. Natl. Acad. Sci. USA*, 105(14): 5453-8 (2008).
Nair et al., Virus-encoded microRNAs: novel regulators of gene expression. *Trends Microbiol.* 14(4):169-75 (2006).
Palliser et al., An siRNA-based microbicide protects mice from lethal herpes simplex virus 2 infection. *Nature*, 439(7072): 89-94 (2006).

(Continued)

*Primary Examiner* — Amy Bowman
(74) *Attorney, Agent, or Firm* — Marshall, Gerstein & Borun LLP

(57) ABSTRACT

The present invention relates to a herpes virus vector which comprises a modified genomic sequence encoding a microRNA (miRNA) against a target sequence. The herpes virus vector may be used as or in a vaccine to prevent and/or treat a disease.

10 Claims, 13 Drawing Sheets

OTHER PUBLICATIONS

Patel et al., Equid herpesvirus (EHV-1) live vaccine strain C147: efficacy against respiratory diseases following EHV types 1 and 4 challenges. *Vet. Microbiol.* 92(1-2):1-17 (2003).
Pfeffer et al., Identification of microRNAs of the herpesvirus family. *Nat. Methods*, 2(4):269-76 (2005).
Pfeffer et al., Identification of virus-encoded microRNAs. *Science*, 304(5671):734-6 (2004).
Rana, Illuminating the silence: understanding the structure and function of small RNAs. *Nat. Rev. Mol. Cell Biol.* 8(1):23-36 (2007).
Randall et al., Interfering with hepatitis C virus RNA replication. *Virus Res.* 102(1)19-25 (2004).
Sabbioni et al., Use of herpes simplex virus 1-based amplicon vector for delivery of small interfering RNA. *Gene Ther.* 14(5): 459-64 (2007).
Saydam et al., Herpes simplex virus 1 amplicon vector-mediated siRNA targeting epidermal growth factor receptor inhibits growth of human glioma cells in vivo. *Mol. Ther.* 12(5): 803-12 92005), 2005.
Skaftnesmo et al., MicroRNAs in tumorigenesis. *Curr. Pharm. Biotechnol.* 8(6): 320-5 (2007).
Stark et al., How cells respond to interferons. *Annu. Rev. Biochem.* 67: 227-64 (1998).
Wiebusch et al., Inhibition of human cytomegalovirus replication by small interfering RNAs. *J. Gen. Virol.* 85(1):179-84 (2004).
Williams, Role of the double-stranded RNA-activated protein kinase (PKR) in cell regulation. *Biochem. Soc. Trans.* 25(2): 509-13 (1997).
Wise et al., Characterization and comparison of chicken U6 promoters for the expression of short hairpin RNAs. *Anim. Biotechnol.* 18(3):153-62 (2007).
Yao et al., Marek's disease virus type 2 (MDV-2)-encoded microRNAs show no sequence conservation with those encoded by MDV-1. *J. Virol.* 81(13):7164-70 (2007).
Yao et al., MicroRNA profile of Marek's disease virus-transformed T-cell line MSB-1: predominance of virus-encoded microRNAs. *J. Virol.* 82(8):4007-15 (2008).
Yoon et al., Inhibition of herpesvirus-6B RNA replication by short interference RNAs. *J. Biochem. Mol. Biol.* 37(3):383-5 (2004).
Yu et al., RNA interference by expression of short-interfering RNAs and hairpin RNAs in mammalian cells. *Proc. Natl. Acad. Sci. USA*, 99(9):6047-52 (2002).
International Search Report and Written Opinion of the International Searching Authority, PCT/GB2009/001471, European Patent Office, dated Oct. 16, 2009.
International Preliminary Report on Patentability, PCT/GB2009/001471, dated Dec. 14, 2010.

* cited by examiner

```
MDV1-mir1 (SEQ ID NO:4)
      U            G           C                              A C A U
C C U   U U U G C U U   U U C A U G U G C G G C A U U A U U A       U
G G   A A G C G A G   A A G U A C G C G U C G U A A U G G         U
    C                A                                     C     A
                                                             C A C MDV1-mir2 (SEQ ID NO:5)
                UG          CC                      G U A A
A A G A A A G U U A U U C U G C G G U A G U C C G U U U     G
U U C U U U C G A U A A G A C G C C G U C A G G C A A G     G
                                                    G     C U
                                                      U U C MDV1-mir3 (SEQ ID NO:6)
        A                      C                           A A U
        A                     AC                                A
G G C U   U G A A A A U G U G A A U C U C C C G C U A G A     A
U U G   A U U U U U A C A C U U G G G G G G C G U C U     A   G
      A                                           U     A A MDV1-mir4 (SEQ ID NO:7)
      UA          UA                C           UC G  U
G A A G U U A U G C U G U C G G A A C C U U C G U G G   G
C U U C A G U A C G A C A G U C U U G G A A G C A C C   A
      UC                          U MDV1-mir5 (SEQ ID NO:8)
                                                    U U U A
      C     U                   U G         G             A
U G A A C   G U A   G C G A U C A C A U     A C A C G     A
G U U U G   C A U   U G C U G G U G U A     U G U G C     A
          U       C                   C   U G       A   U
                                                      U A C A MDV1-mir6 (SEQ ID NO:9)
      U                     C           U G U         U G A C
                                                                A
G A A A A C U G U U G U U C G U A G     U C U C G             C
C U U U U G A C A G U A A G C G U C     A G A G C             U
                        A           C C U             U C A A MDV1-mir7 (SEQ ID NO:10)
                                                    C U C U C C
      U           G           C           U                     U
A A C U G U   A U C U C G   G G A G A U C   C G A               A
U U G A C A   U A G A G C   U C U C U A G   G C U               C
            U             A             A         C           C
                                                    A A C G A MDV1-mir8 (SEQ ID NO:11)
                                                  U C U A U C
      C                     U U         U     A             G
A A A   C U A U U G U U C U G U G G     G G U U   C G         U
U U U   G A U A A C A A G G C A U C     C C A G   G C         U
      U                             U             U         C
                                                      U     C
                                                        C A U G C
```

FIG. 1A

MDV1-mir9 (SEQ ID NO:12)
```
       G          CUUC              C           U
GCG UUUUUCU      C   CCCCGGAGUU  ACUGUA  C
CGU AAAAAGG      GGGGCCUCAA  UGGCAU G
   G        A C   A       A  UU
```

MDV1-mir10 (SEQ ID NO:13)
```
                                      A U C U
    C                                      C
UGG  GUUGUCUCGUAGAGGUCCAG
GUU  CAAUAGAGCAUCUCUAGGUU       U
   UGA                    A  CA  G U C C
                           A    A
                           G   A
                            C U C
```

MDV1-mir11 (SEQ ID NO:14)
```
   UU                                G
AAA UUCCUUACCGUGUAGCUUAGA  C UC  G
UUU AGGGAUGGUACAUUGAGUUU    AG A
         C                UAUCA  A
```

MDV1-mir12 (SEQ ID NO:15)
```
                                  G U C
GAUCA A GGCCCUCCGUAU A AUGUAAAU      C
CUAGU  UUGGGAGGCAUA  UACGUUUG     A
     C              A         G A A
```

MDV1-mir13 (SEQ ID NO:16)
```
            G A      C G          A C
AGUUUUCCAGGA  UUUCC   GUUUCG       U
UCAAAGGGUCCU  AAGG   CGAAGC      C G
  UA         G C    U A
```

FIG. 1A cont'd

SEQ ID NO:17
F1mdv5 →
gcggagttatatgttacgcggttcccagcctataagaatcgtggtgttggcgccaaa Aaatgcgcgccaacaaaaaggcgccaaaaaattgcgcgccattgtttggcgccttttt Tctgcgccgttttcaaaatcgcgccataccaatttcaaagttcccgccatttggcca acacgctattatccctgcatgatcttctttaattggacgacattcctcgattcccga
                                    *PvuI*
tccacatatccagtgacaggagttcggaataaacgttgtgatacg*cgatcg*agtttt
               miR-8 →
cgtggcatattcctacggaaacctattgttctgtggttggtttcgatctatcgttct
           ← miR-8*
cgtactgcgtgacctctacggaacaatagttttccaggagatttcccggtttcgact
              miR-6* →
gccgaagcatggaaacgtcctgggaaaatctgttgttccgtagtgttctcgtgacac
            ← miR-6
taactcgagatccctgcgaaatgacagttttctctgggaattacatcgtcctgattg tcgcgacatggaatggaagcctcataggaagaactcgatgtgatgatgctctctagc
                miR-7 →
caagagagccgcgaacgctccaaggagaactgttatctcgggagatcccgatctct
             ← miR-7*
cctaccagcaactcgagatctctacgagattacagtttttgggggaaatgtgtcctc
        *HindIII*        miR-10 →
agaactgcttaatcgtag*aagctt*cctagtggatggcgttgtctcgtagaggtccag atctctcctgttggcaactcgaaatctctacgagataacagtttgtctaggaaactt tcctcccaactaaagagcgatgacttaggaagtaaacgtgccctcatcaccgcccttt acacactgctagtcattcatgtacattgcgattgtgccttggtgcggggcggttcct aggcaccatttatcttgtattcctgtacatcccctccttaatactttaattggagcc
                ← R2mdv5

FIG. 3

```
Renilla luciferase siRNA:    5'-(ACGT)GCUUGGACUCCUUCAUCAAC(UACU)-3'
(SEQ ID NO:18)    (mature)    3'-(TGCT)CGACCUGAGGAAGUAGUUG(AUGA)-5' miR-7:  5' AACGCTCCAAGGAGAAC TGTTATCT GGGAGATCC CGA TCTCTCCTACCAGCAAC TCG AGATCTCTACGAGATTACA GTTTTTGGGGGA
(SEQ ID NO:19)

MDV1-miR-M7 (SEQ ID NO:10)
         U  U C
      C       C    U     A
AACUG  AUCUCG  GGAGAUC  CGA    C
UUGACA UAGAGC  UCUCUAG  GCU    C
    A U     A A      A  A  ACGA pN1-miR-LAT-HPC miR-7 MCS (SEQ ID NO:1)

AACGCTCCAAG|GAGA ACTGGCAGGTGCGATCCGCACCTGCAGTT|TTTG GGGGA
                                   BamHI   AarI
TTGCGAGGTTC CTCT|TGACCGTCCACGCCTAGCGTGGACGTCAA AAAC|CCCCT
                                   AarI miR-7-hRluc-19
5'-GAGAACGTTGATGAAGGAGTCCAGCCGGAUCUCUCUCU           (SEQ ID NO:20)
   :|:|||||| ||||| |||||| |||
3'-UUUUGCAAGUACUUCAAGGUCAGCUCAACGACC                (SEQ ID NO:21)

miR-7-hRluc-19-T:5'-GAGAAC GTTGATGAAGGAGTCCAGCCGGA TCTCTCCTACCAGCAAC TCGACTGGACTACTTCATGAAC GTT -3' (SEQ ID NO:22)
                 Comp    3'-    TG   CAACTACTTCCTCAGGTCGGCT AGAGAGGATGGTCGTTG AGCTGACCTGATGAAGTACTTG CAAAAAC -5'(SEQ ID NO:23)

miR-7-hRluc-19-b:5'-CAAAAAC GTTCATGAAGTAGTCCAGTCGA GTTGCTGGTAGGAGAGA TCGGCTGGACTCCTTCATCAAC GT -3' (SEQ ID NO:23)

miR-7-hRluc-22
5'-GAGAACGTTGATGAAGGAGTCCAGCCGGCTCTCTCU           (SEQ ID NO:24)
   :|:|||||| ||||| |||||| |||
3'-UUUUGCAAGUACUUCAUCAGGUCAGGCCAACGACC            (SEQ ID NO:25)
```

FIG. 4

```
miR-7-hRluc-22-t:5'- GAGAAC GTTGATGAAGGAGTCCAGCTCG TCTCTCCTACCAGCAAC CGAACTGGACTACTTCATGAAC GTT -3'(SEQ ID NO:26)
Comp            3'-    TG CAACTACTTCCTCAGGTCGAGC AGAGAGGATGGTCGTTG GCTTGACCTGATGAAGTACTTG CAAAAAC -5'(SEQ ID NO:27)

miR-7-hRluc-22-b:5'- CAAAAAC GTTCATGAAGTAGTCCAGTTCG GTTGCTGTAGGAGAGA CGAGCTGGACTCCTTCATCAAC GT -3'(SEQ ID NO:27)

miR-7-hRluc-19'
5'- GAGAACUGUGUUGAUGAAGGAGUCCAGCUCUCUCCU      (SEQ ID NO:28)
    :|:||||||  ||||||  |||||||  |||
3'- UUUUUGACAGAACUACGUCCUCAGAUCGAACGACC  A    (SEQ ID NO:29)

miR-7-hRluc-19 -t:5'- GAGAAC TGTGTTGATGAAGGAGTCCAGC TCTCTCCTACCAGCAGC GCTAGACTCCTGCATCAAGACA GTT -3'(SEQ ID NO:30)
Comp            3'-    TG ACACAACTACTTCCTCAGGTCG AGAGAGGATGGTCGTTG CGATCTGAGGACGTAGTTCTGT CAAAAAC -5'(SEQ ID NO:31)

miR-7-hRluc-19 -b:5'- CAAAAAC TGTCTTGATGCAGGAGTCTAGC GTTGCTGGTAGGAGAGA GCTGGACTCCTTCATCAACACA GT -3'(SEQ ID NO:31)
```

FIG. 4 cont'd

VECTOR

This application is the U.S. National Stage of International Application No. PCT/GB2009/001471, incorporated by reference, filed Jun. 11, 2009, which claims the priority benefit of Great Britain Application No. 0810912.6, filed Jun. 13, 2008.

FIELD OF THE INVENTION

The present invention relates to a herpesvirus vector. In particular, it relates to a herpesvirus vector which comprises a modified genomic sequence capable of encoding a microRNA (miRNA) against a target sequence.

BACKGROUND TO THE INVENTION

Infectious diseases caused by existing and new emerging viruses pose a major threat to human and animal health, in both developed and developing nations. Although some degree of control is achieved by using vaccines and antiviral drugs, such approaches are only effective for a small proportion of these viruses. Recent advances in medicine and molecular biology have uncovered novel approaches and technologies that could be harnessed in the fight against infectious diseases. The discovery of RNA interference (RNAi) as an evolutionarily conserved and sequence-specific gene silencing mechanism in eukaryotes (Fire, A. et al. (1998) Nature 391, 806-11) has paved way for developing RNAi as a powerful therapeutic tool against pathogenic agents such as viruses.

RNA interference (RNAi) is a naturally occurring cellular mechanism of gene suppression that functions in both plants and animals. The conserved RNAi pathway involves the processing of double stranded RNA (dsRNA) duplexes into 21-23 nucleotide (nt) molecules, known as small interfering RNAs (siRNA), to initiate gene suppression (Hannon, (2002) RNA interference. Nature 418, 244-51). In mammalian systems, the cellular processing of long dsRNA can induce an interferon (IFN) mediated antiviral defence mechanism that ultimately leads to non-specific translational shutdown and apoptosis (Stark et al., (1998) Annu Rev Biochem 67, 227-64, Williams, (1997) Biochem Soc Trans 25, 509-13). However, this non-specific cellular activity can be circumvented by the direct transfection of in vitro synthesized siRNAs of up to 30 nucleotides (nt) in length (Elbashir et al., (2001) Nature 411, 494-8). Since this discovery, the development of DNA-based vectors for expression of short hairpin RNA (shRNA) molecules that are processed within the cell to produce active siRNA molecules has progressed rapidly (Brummelkamp et al., (2002) Science 296, 550-3, Yu et al., (2002) Proc Natl Acad Sci USA 99, 6047-52). Such shRNA expression vectors often feature promoters of a small class of RNA polymerase III (pol III) promoters such as U6 and 7SK. There has been a total of five separate U6 promoters described from the human genome (Domitrovich & Kunkel, Nucleic Acids Res 31, 2344-52 (2003), each loci displayed differential transcriptional activities, a finding which has also been seen for the chicken (Kudo & Sutou (2005) J Reprod Dev 51, 411-7, Wise et al., (2007) Anim Biotechnol 18, 153-62) and the cow (Lambeth et al., (2006) Anim Genet 37, 369-72).

While initial demonstrations of RNAi in mammalian cells showed suppression of cellular transcripts, more recently both siRNAs and shRNA have been shown to suppress replication of a number of viruses in vitro and in vivo. For example, the efficient inhibition of human pathogens such as hepatitis C virus (Randall & Rice, (2004) Virus Res 102, 19-25), human immunodeficiency virus-1 (Coburn & Cullen, (2002) J Virol 76, 9225-31) and influenza A (Ge et al., (2003) Proc Natl Acad Sci U S A 100, 2718-23), as well as livestock viruses such as foot and mouth disease virus (Chen et al., (2004) J Virol 78, 6900-7, Liu et al., (2005) Virology 336, 51-9) by RNAi have been described. The use of RNAi to inhibit the replication of several herpesviruses has also been reported, including murine herpesvirus 68 (Jia & Sun, (2003) J Virol 77, 3301-6), Epstein-Barr virus (Chang et al., (2004) Gen Virol 85, 1371-9) HSV-1 (Bhuyan et al., (2004) J Virol 78, 10276-81) herpesvirus-6B (Yoon et al., (2004) J Biochem Mol Biol 37, 383-5), human cytomegalovirus (Wiebusch et al., (2004) J Gen Virol 85, 179-84), Kaposi sarcoma-associated herpesvirus (Godfrey et al., (2005) Blood 105, 2510-8), duck herpesvirus (Mallanna et al., (2006) Virus Res 115, 192-7) and HSV-2 (Palliser et al., (2006) Nature 439, 89-94).

These studies have involved the introduction of synthetic siRNA, or the genetic transfer of DNA expression cassettes capable of producing siRNA or shRNA in human cells. While this approach may give valuable information about the mechanism of RNAi using cells in culture, it can be difficult to achieve the same effect in vivo. There are difficulties associated with expressing the siRNA in the target cell type and achieving sufficient and sustainable levels of expression.

Although the specific and effective nature of RNAi is potentially a highly powerful therapeutic tool, sustainable long-term target gene knockdown still remains a hurdle for widespread therapeutic use of RNAi. Delivery of siRNAs through the use of recombinant viral vectors such as adenoviruses, adeno-associated viruses (AAV) and lentiviruses can overcome some of these problems. However, concerns on the safety of some of these vectors and over-saturation of the RNAi pathway due to higher expression levels of siRNAs are to be tackled (Aagard and Rossi (2007) Adv. Drug Delivery Reviews 59, 75-86).

There is thus a need for an improved RNAi delivery mechanism giving sustainable long-term levels of expression of RNAi in vivo.

SUMMARY OF ASPECTS OF THE PRESENT INVENTION

The present inventors have found that it is possible to modify the endogenous miRNA cluster of herpesviruses, such as Marek's disease virus (MDV) to express miRNA against a target gene(s). As herpesvirus miRNAs are heavily expressed throughout the herpesvirus lifecycle, steady high levels of expression of the modified miRNA can also be achieved.

In a first aspect, the present invention provides a herpesvirus vector which comprises a modified genomic sequence encoding a microRNA (miRNA) against a target sequence.

The modified miRNA may be a therapeutic miRNA, and the vector useful to prevent and/or treat a disease.

The miRNA may be against a target sequence from an infectious pathogen, such as a virus. The miRNA may be capable of silencing the expression of a gene from the infectious pathogen, which may inhibit for example, replication of or infection by the infectious pathogen.

The infectious pathogen may be a herpesvirus. As the herpesvirus vector is based on a herpesvirus, it is likely to follow the same route of infection and access the same tissues as the infectious pathogen. This has the advantage that the miRNA will be produced at the correct sites in the body.

If the herpesvirus vector encodes a miRNA against a target sequence from the pathogenic herpesvirus on which the vector is based, there is the added advantage that the vector may act as a traditional vaccine, such as a live attenuated vaccine stimulating an immune response against the infectious pathogen.

If the target sequence within the infectious pathogen, or a sequence having a high degree of identity thereto, occurs in the herpesvirus vector, it may be preferable to modify the herpesvirus vector so that the miRNA does not silence the vector itself.

The herpesvirus vector of the first aspect of the invention may be based on a Marek's disease virus (MDV). The present inventors have shown that there are 13 miRNAs in MDV-1 (Yao et al (2008) J Virol 82: 4007-15) and 17 in MDV-2 (Yao et al (2007) J. Virol 81:7164-70), most of which are expressed as clusters. For example, the herpesvirus vector may comprise a modified miR-M7 sequence.

The vector of the first aspect of the invention may be capable of expressing a plurality of modified miRNAs. For example, the vector may comprise a plurality of modified genomic sequences each encoding a modified microRNA. The miRNAs may be against target sequences in the same target gene or different target gene. If the miRNAs are directed against a plurality of target genes, they may be genes within the same target pathogen.

In viruses such as Marek's disease virus (MDV) multiple miRNAs are expressed as polycistronic miRNA transcripts, facilitating the coexpression of multiple modified miRNAs.

The expression of multiple miRNAs is particularly advantageous for use against escape-prone viral pathogens, such as HIV. Minor sequence changes in the target sequence, sometimes even a single point mutation, can be sufficient to overcome RNAi-mediated inhibition, due to the exquisite substrate-specificity of RNAi. Hence, HIV can escape inhibition by RNAi if mutation occurs within the target sequence. This risk is greatly reduced by simultaneous expression of a plurality of miRNAs, as escape would then theroretically involve mutation of all of the target sequences.

In a second aspect, the present invention provides a method for producing a vector according to the first aspect of the invention, which comprises the step of introducing one or more mutations in the sequences encoding the strands forming the stem of the stem-loop structure of a pri-miRNA encoded by the herpesvirus vector genome.

Where the creation of the desired miRNA-encoding sequence would involve multiple point mutations, it may be simpler to replace the mi-RNA sequence with a foreign sequence.

In order to ensure the pre-miRNA is efficiently cleaved by dicer, the mutations may be designed so that the modified pre-miRNA retains the structural features of the natural pre-miRNA.

The method of the second aspect of the invention may comprise the following steps:
 (i) amplification of the genomic miRNA of a herpesvirus;
 (ii) mutation of the miRNA;
 (iii) generation of a mutant clone of the herpesvirus by BAC mutagenesis to produce a herpesvirus vector which comprises a modified genomic sequence, capable of encoding a micro RNA (miRNA) against a target sequence.

In a third aspect, the present invention provides a vaccine comprising a herpesvirus vector according to the first aspect of the invention. The vector or vaccine of the invention may be used to prevent and/or treat a disease.

The disease may be a viral disease. The disease may, for example, be selected from the following group: HIV, hepatitis viruses, Respiratory Syncytial viruses (RSV), Marek's disease, avian influenza, infectious bursal disease, chicken anaemia, Newcastle disease, infectious bronchitis, Reovirus infections, infectious laryngeotracheitis and fowl pox.

Alternatively, the target sequence could be any host gene whose expression could be specifically silenced by the herpesvirus expressing the modified miRNA against that gene in a cell type-specific manner depending on the tropism of the herpesvirus. For example, neurotropic herpesviruses such as HSV-1 could be used to silence genes involved in neurologic disorders, or herpesviruses expressing modified miRNAs capable of specific gene silencing could be used as therapeutic vaccines in conditions such as cancer.

DESCRIPTION OF THE FIGURES

FIG. 1A shows the secondary structures of MDV-1 pre-miRNAs predicted using the MFOLD algorithm. The mature miRNA strands are shown in red.

FIG. 3 shows the nucleotide sequence of the MDV-1 miR-6-7-8-10 cluster. The sequences of the miRNA strands of each of the miRNAs are shown in colour.

FIG. 4 is a schematic diagram outlining the strategy for modifying the MDV-1 miR-M7 sequence as siRNA against the Luciferase gene. All sequences in red are native miRNA sequences, black sequences are luciferase shRNA sequences, and blue sequences are complementary strands and are for visualisation only.

DETAILED DESCRIPTION

Herpesvirus Vector

Figure 1:
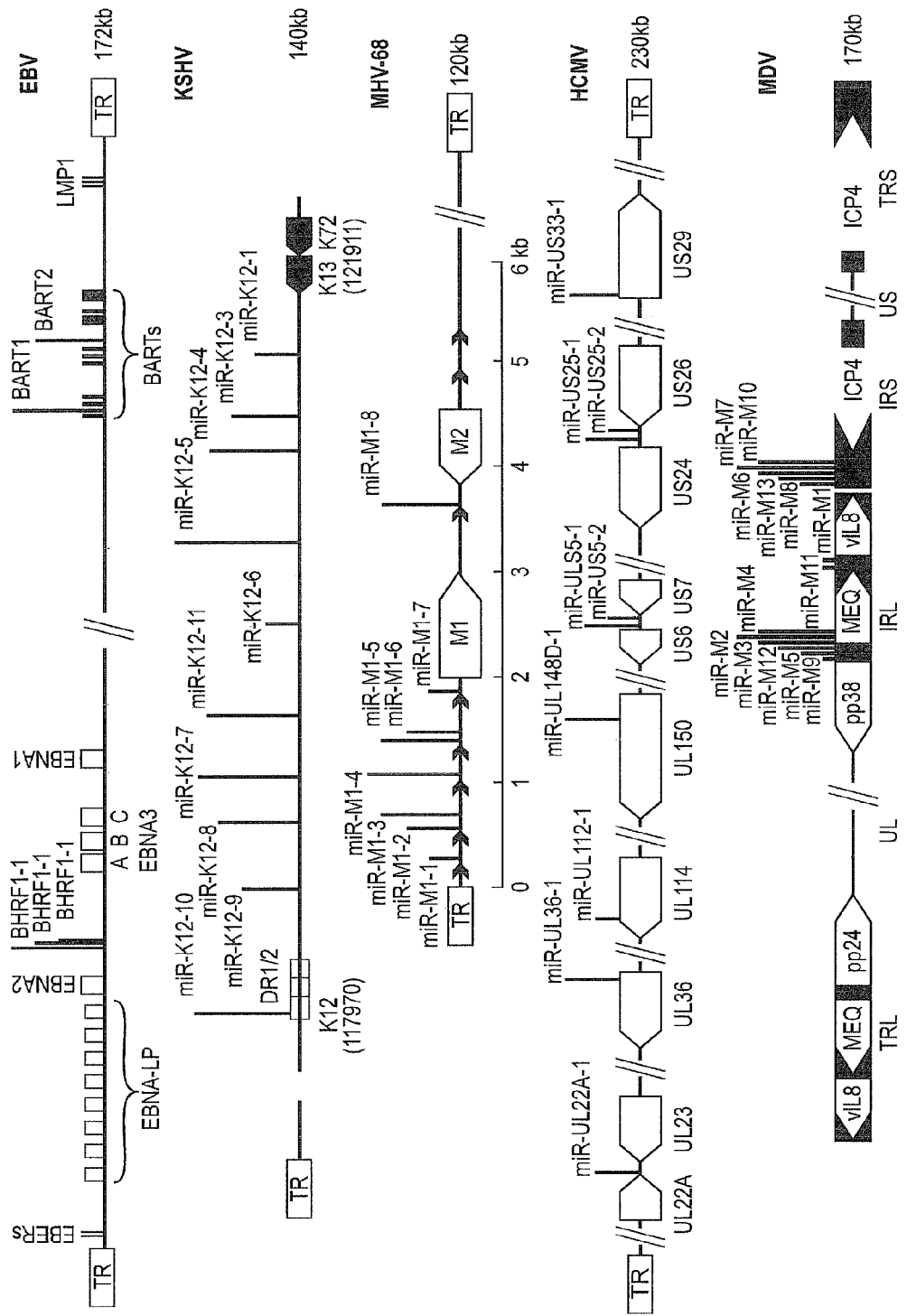
FIG. 1 shows the details and the names of the miRNAs encoded by different herpesviruses.

The term "vector" is used to indicate a herpesvirus which is capable of delivering a nucleotide of interest NOI) to a target cell. In the context of the present invention the NOI is, or is capable of producing an miRNA.

The NOI may be, for example, a genomic sequence capable of encoding a pri-miRNA, a priMRNA sequence, a pre-miRNA sequence, or a mature miRNA.

The herpesvirus vector may be derivable from a herpesvirus, for example, MDV, HVT, HSV-1, HSV-2, VZV, EBV or CMV (see below).

Where a vector is "based on" a particular herpesvirus, it indicates that the vector is derivable from the wild-type virus, but may be modified, for example to reduce its virulence. The vector may, for example, be attenuated (see below) and/or modified to increase its immunogenicity or target it to a particular tissue.

The herpesvirus expressing the modified miRNA may silence expression of a target gene in a cell type-specific manner depending on the tropism of the herpesvirus.

This means that it is possible to select a herpes virus, based on its cell tropism, to silence expression of a target gene in particular cells of interest.

Table 1 shows herpesviruses which encode miRNAs and their cell tropism.

TABLE 1

| Name of the herpesvirus | Number of miRNAs | Cell tropism known |
|---|---|---|
| Epstein Barr virus (EBV) -Human | 23 | Lymphocytes |
| Herpes Simplex Virus 1 (HSV-1) -Human | 1 | Central nervous System (neurons) |
| Human cytomegalovirus (HCMV) -Human | 11 | Smooth muscle, myeloid cells, Endothelial cells |
| Kaposi sarcoma-associated herpesvirus (KSHV) -Human | 13 | B & T Lymphocytes |
| Marek's disease virus type 1 (MDV-1) -Chicken | 13 | T lymphocytes |
| Marek's disease virus type 2 (MDV-2) - Chicken | 17 | T lymphocytes |
| Mouse cytomegalovirus (MCMV) -Murine | 18 | Mouse endothelial cells, neurons Dendritic cells |
| Mouse gammaherpesvirus-68 (MHV-68) - Murine | 9 | Epithelial cells, B lymphocytes, Macrophages and. Dendritic cells |
| Rhesus lymphocryptovirus (LCV) - Primates | 16 | Primate epithelial cells and B lymphocytes |
| Rhesus monkey rhadinovirus -Primates | 7 | Epithelial cells and B lymphocytes |

Other herpesviruses potentially encoding miRNAs

HHV3 or Varicella Zoster virus (VZV) in human- lymphocytes, dorsal root ganglia, skin
Alcelaphine herpesvirus-1 Malignant catarrhal fever in cattle - lymphocytes/lymphoid organs
Bovine herpesvirus-1 (BHV-1) - Herpesvirus causing infectious bovine rhinotracheitis (respiratory system)
Bovine herpesvirus-4 (BHV-4) - Gammaherpesvirus- lymphoid cell tropism
Equid herpesvirus -1, -2 and -4 (EHV)- Central nervous system in horses
Infectious laryngeotrachieitis (ILTV)- Respiratory tract in chicken
Psittacid herpesvirus (PsHV)- Respiratory tract in chicken RNAi There are two major classes of small RNAs that are characteristic of RNAi: (i) first is the small interfering RNAs (siRNAs) which are 21-23 fully base-paired duplexes which interact with perfect base-pairing with a region of the messenger RNA transcript triggering its specific degradation through the RNA-induced silencing complex (RISC) (Rana, T. M. (2007) Nat Rev Mol Cell Biol 8, 23-36). The technology and application of silencing of specific genes and viruses using siRNAs is progressing steadily and several trials are in progress (Aagaard, L. & Rossi, J. J. (2007) Adv Drug Deliv Rev 59, 75-86; de Fougerolles et al (2007) Nat Rev Drug Discov 6, 443-53). These are usually induced by polymerase III promoters (e.g. U6, H1 etc) from short hairpin RNA (shRNA) expression vectors. (ii) Second is the microRNAs (miRNA) which are 21-23 base duplexes that are usually base-paired incompletely forming partial duplexes within the 3' untranslated region (UTR) of targeted transcripts through RISC resulting in the inhibition of translation. Several miRNAs have been identified in different species (Griffiths-Jones et al (2008) Nucleic Acids Res 36, D154-8). These are thought to be expressed and regulated similar to the protein-coding genes from polymerase II promoters, first as long primary transcripts (pri-miRNAs) (Lagos-Quintana, M. et al. (2002) Curr Biol 12, 735-9). The pri-miRNA is cleaved by the nuclear Drosha-DGCR8 complex to produce pre-miRNA, which are further processed in the cytoplasm to mature miRNA duplex. The expression of many of these miRNAs is restricted to specific cell lineages and developmental stages, and recent data suggest that they exert profound influence on gene regulation in a wide range of conditions and diseases including cancer (Skaftnesmo et al (2007) Curr Pharm Biotechnol 8, 320-5).

miRNA

Figure 6:
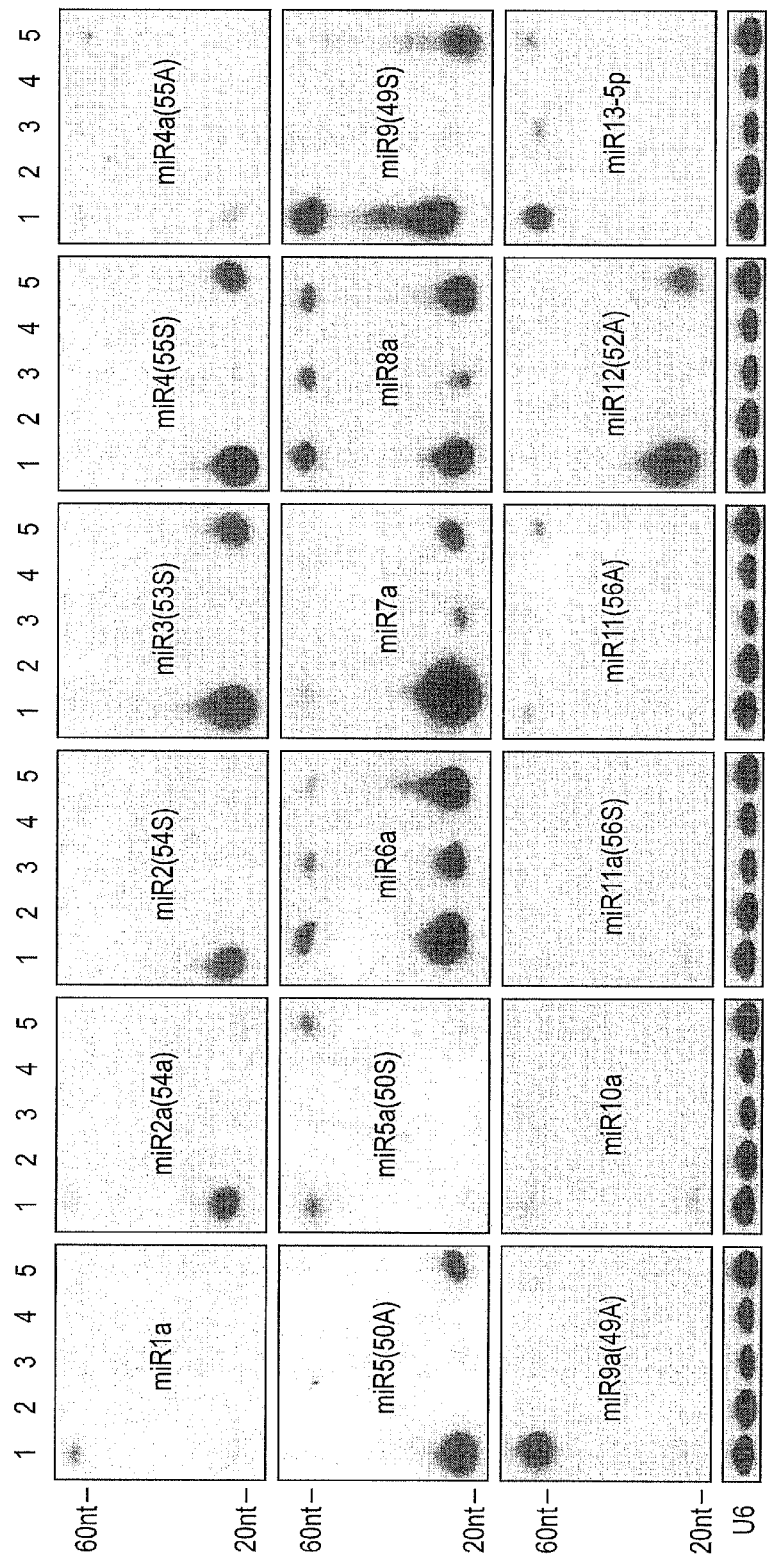
FIG. 6 shows Northern Blotting analysis showing the expression of miRNAs encoded by MDV-1.
Figure 7:
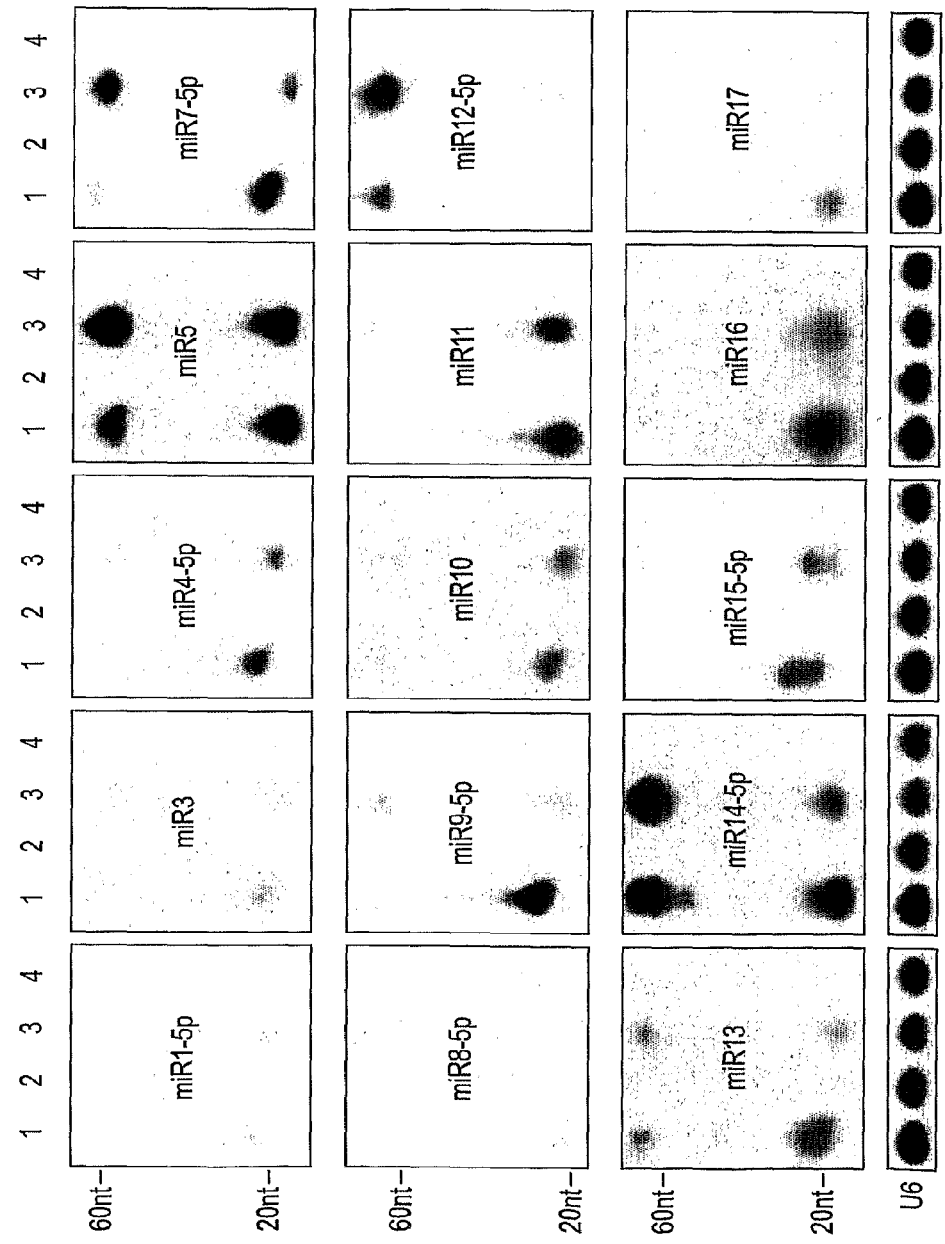
FIG. 7 shows Northern Blotting analysis showing the expression of miRNAs encoded by MDV-2.
Figure 8:
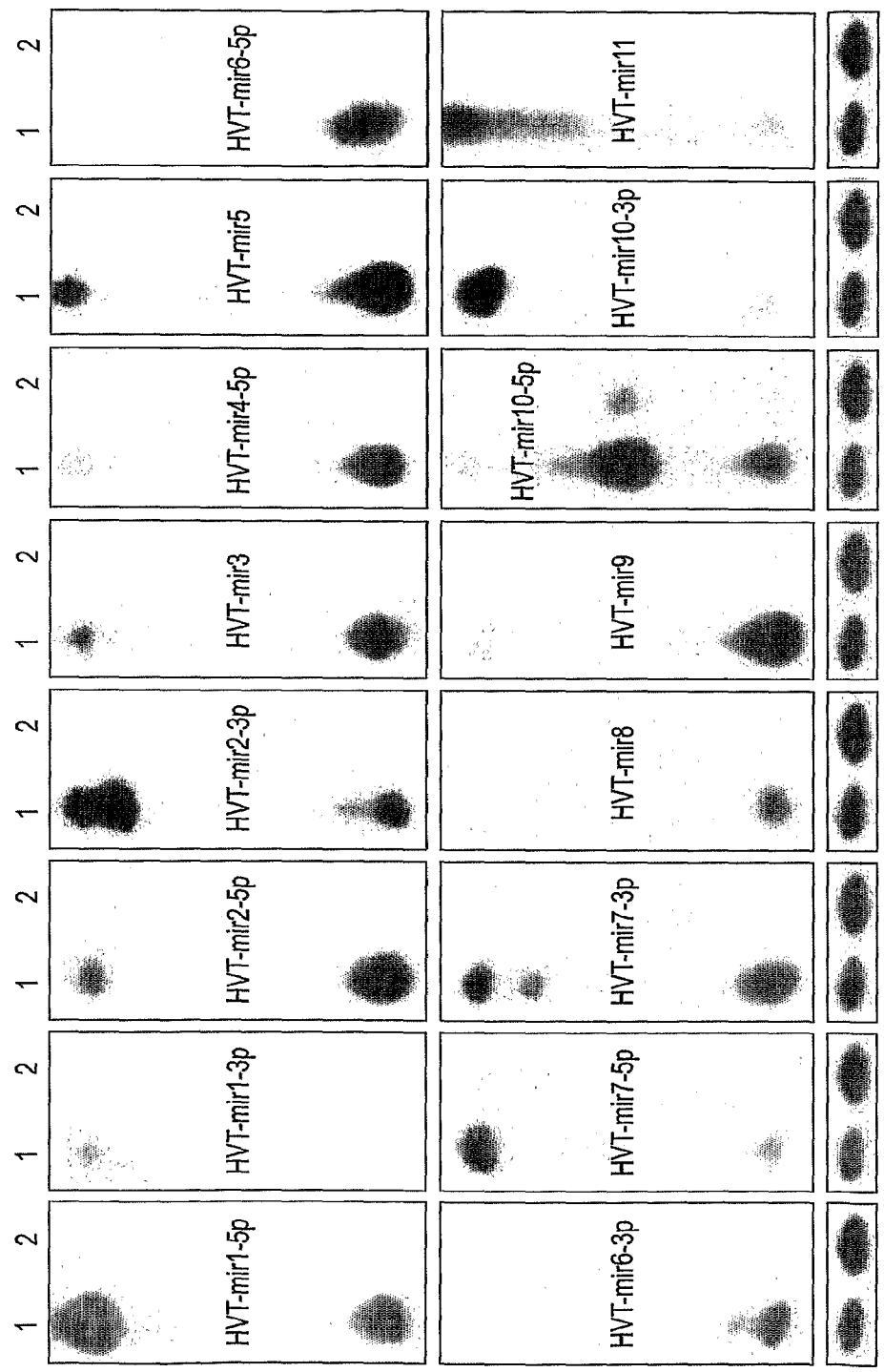
FIG. 8 shows Northern Blotting analysis showing the expression of miRNAs encoded by HVT strains of MDV.
Figure 9:
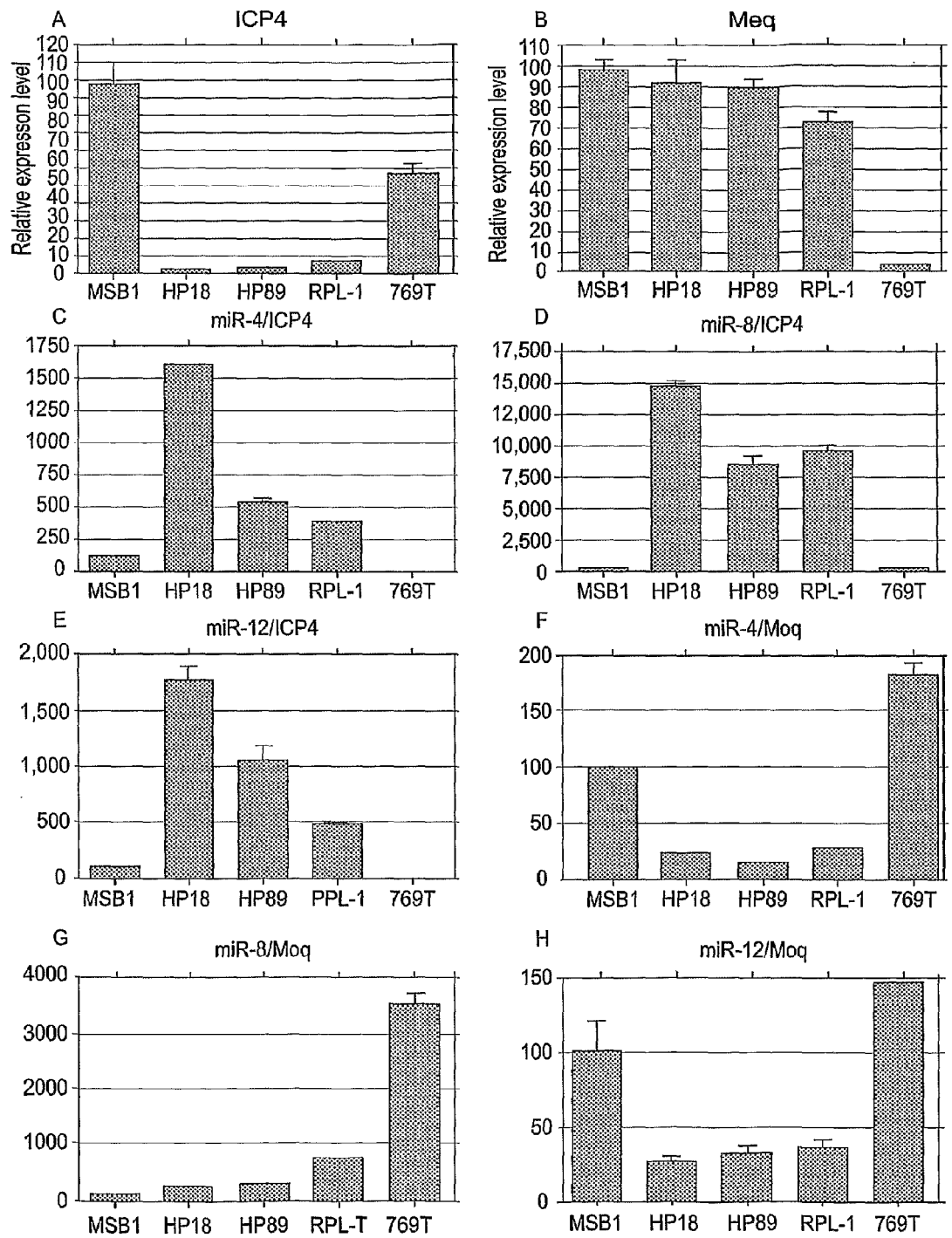
FIG. 9 shows quantitative RT-PCR measuring the levels of ICP4, Meq and miR-4, miR-8 and miR-12 transcripts in MDV-transformed cells.

The first discovery of virus-encoded miRNAs was made in the EBV genome (Pfeffer, S. et al. (2004) Science 304, 734-6). Since then, several virus-encoded miRNAs have been identified (Pfeffer, S. et al. (2005) Nat Methods 2, 269-76; Cullen, B. R. (2006) Nat Genet 38 Suppl, S25-30; Nair, V. & Zavolan, M. (2006) Trends Microbiol 14, 169-75) with herpesviruses accounting for nearly all (124/127) virus-encoded miRNAs in miRBase (Griffiths-Jones et al (2008) Nucleic Acids Res 36, D154-8). The present inventors have reported the identification of several novel miRNAs in Marek's disease virus (MDV), alphaherpesviruses belonging to the genus Mardivirus in the family Herpesviridae. These include 13 miRNAs in MDV-1 (Yao, Y. et al. (2008) J Virol 82, 4007-15), 17 in MDV-2 (Yao, Y. et al. (2007) J Virol 81, 7164-70) and 11 in HVT (unpublished). Most of these miRNAs are expressed as clusters and the genomic structure of these miRNAs is provided in FIG. 1. The majority of these miRNAs are expressed at very high levels in infected cells/tissues as shown by Northern blotting (FIGS. 6, 7, and 8), and qPCR analysis (FIG. 9).

The present inventors have found that it is possible to modify the endogenous genomic miRNA-encoding sequence in a herpesvirus miRNA cluster so that is expresses a modified miRNA. This modified miRNA may be complementary to a target sequence of interest.

Thus in a first aspect, the present invention provides a herpesvirus vector which comprises a modified genomic sequence encoding a microRNA (miRNA) against a target sequence.

The term "modified" is used to indicate that the genomic miRNA-encoding sequence comprises one or more mutations, such that it produces a modified miRNA which is different from the miRNA sequence which would have been produced, had the genomic sequence not been mutated. The genomic miRNA-encoding sequence is endogenous, in the sense that its sequence, prior to modification, occurs naturally within the herpesvirus genome.

The "modifications" i.e. mutations in the genomic miRNA encoding sequence, are made in the sequences encoding the two strands which form the stem of the stem-loop structure. Symmetrical mutations should be made in each strand-encoding sequence, so the correct stem-loop structure is produced in the pri-miRNA.

The miRNA produced by the vector of the present invention is typically between 20 and 25, for example 21-23 base pairs in length.

Target Sequence

The target sequence may be part of a target gene.

Where the disease is an infectious disease, the target sequence or target gene may be a target sequence or target gene from an infectious pathogen.

Alternatively, the target sequence or target gene may be a host gene whose expression is desired to be reduced or silenced. For example, it may be desirable to silence expression of a particular gene associated with the pathogenic immune response generated during an allergy or autoimmune disease. Also, in cancer, it may be possible to silence expression of gene(s) involved in abnormal cell proliferation.

Herpesviruses express miRNA against host gene as part of their normal biology. In the context of the present invention, where the miRNA is against a target sequence from a host gene, the host gene is different from the gene usually silenced by that particular miRNA. The miRNA has been modified to target a selected host gene, not normally silenced by that miRNA.

The target sequence or target gene may alternatively be a gene of interest in an animal model. In this way, the technology may be used to investigate the effect of silencing a host gene, in order to provide information about the function of the gene. In a mouse model, the muring herpesviruses MHV-68 and MCMV may be useful in this application as they target lymphocytes, macrophages, dendritic cells and endothelial cells and express high levels of miRNA in these cells.

The target sequence is a sequence to which the miRNA binds. The target sequence may be RNA, in particular messenger RNA (mRNA).

Where the target sequence is from an infections pathogen, the target sequence or target gene may be an essential sequence, without which the infectious pathogen cannot perform an essential function, such as replication or infection of the host. If expression (i.e. transcription or translation) of an essential target sequence is blocked, the pathogen may not be viable. In MDV, studies have shown that the gB envelope glycoprotein is essential for MDV replication (Schumacher et al., 2000), and is likely to be involved in viral spread. Another attractive candidate is the replication gene UL29 as this is a highly conserved gene that encodes the single-stranded DNA binding protein that has already proved to be an excellent candidate for RNAi directed against HSV-2 (Palliser et al., 2006).

The vector may be able to express a plurality of miRNAs each against a different target sequence. The target sequences may be different sequences within the same target gene or within different target genes. Where two or more miRNAs are expressed against the same target gene, they may have an "additive effect" causing enhanced silencing of the target gene.

The term "against" means that the miRNA specifically recognises the target sequence. The miRNA has a complementary nucleotide sequence to the target sequence. Typically the miRNA will be 100% complementary to the target sequence. However, it is thought that miRNAs, unlike siRNAs derived from long dsRNA precursors, can tolerate a degree of incomplete base pairing. Hence the miRNA may have three, two or preferably one mismatch with the target sequence.

The miRNA may silence the expression of the target sequence or target gene. The expressed miRNA is incorporated into the RNA-induced silencing complex (RISC) where it pairs with the target sequence. Where the target sequence or target gene is mRNA, the RISC may then cause post-transcriptional gene silencing, where specific base pairing causes degradation of the target sequence by argonaute, the catalytic component of the RISC complex. In connection with this aspect, the target sequence ma be within the 3' UTR of the mRNA.

The RISC complex may alternatively or also affect transcription of a target sequence (which may therefore be a DNA sequence) by causing epigenetic changes to a gene, such as histone modification and DNA methylation, which affects the degree the gene is transcribed.

The term "silenced" indicates that expression of the target sequence or target gene is partially or completely reduced, compared to the level of expression which would be seen in the absence of the miRNA. Expression of the target gene may be silenced by, for example at least 50, 60, 70, 80, 90 or 95%.

Once a target gene has been identified, it is possible to identify candidate miRNA sequences using techniques known in the art, such as using the siRNA design platform from Eurogenetec.

One of the advantages of the vector of the present invention is that the miRNA is produced from the herpesvirus vector genome in the same way as an endogenous miRNA sequence, and can then silence the target gene using the regulatory mechanisms of the natural herpesvirus loci.

In the natural miRNA maturation pathway, the primary miRNA (pri-miRNA) is transcribed from its genomic location and cleaved by the microprocessor complex, which comprises Drosha and DGCR8. The resulting pre-miRNA is actively transported to the cytoplasm by transportin 5, where the pre-miRNA undergoes further processing into the mature miRNA by Dicer and its co-factors, PACT and TAR RNA binding protein TBRP. The mature niRNA is then loaded on to the RISC complex.

Modification of the miRNA encoding sequence should be designed to retain any sequence and structural features needed for efficient recognition by Drosha, DGCR8, transportin 5, Dicer and its co-factors, or the RISC complex. For example, in order to ensure the pre-miRNA is efficiently cleaved by dicer, deliberate mismatches may be included in the sequences encoding the two strands of the basepaired stem may be modified to mimic structural features of the natural pre-miRNA.

In the context of the present invention the "natural" pri-miRNA, pre-miRNA or miRNA sequence is that which would have been produced by the herpesvirus in the absence of any modification.

Vaccine

The present invention also relates to a vaccine. A vaccine is an antigenic preparation used to establish immunity to a disease.

The herpesvirus vector itself will induce an immunological response when administered to a subject. This immune response may also be valuable in treating or preventing the disease. For example, where the disease is an infectious disease, the immune response may also help to control or eliminate infection by the pathogen.

The herpesvirus vector of the first aspect on the invention may be based on a herpesvirus which is already used as a vaccine.

It may be based on an attenuated herpesvirus i.e. a herpesvirus which has been cultivated under conditions that reduce its virulence.

Viruses may be attenuated by passage of the virus through a foreign host, such as by tissue culture or passage through embryonated eggs or live animals. In such methods, the initial viral population is applied to the foreign host. There is selection pressure for any mutant having an increased capacity to infect the new host. This mutant will normally have a lower virulence in the original host, but retains the capacity of the original virus to induce an immune response, making it an attractive vaccine candidate.

It has been found that the miRNA clusters of herpesviruses are conserved in the attenuated vaccine strains.

Live attenuated vaccines are widely used for immunisation against many viral infections, particularly in veterinary medicine, such as against Marek's disease (see below).

In live vaccination it is also possible to use a microorganism which does not give rise to the target disease, but which causes the generation of a protective immune response to the target disease. The classical observation by Jenner in 1796 that exposure to cowpox provided protection against smallpox was based on this type of immune response.

In Marek's disease, herpes virus of turkey (HVT) can be used to induce an immune response which will protect against Marek's disease virus (MDV).

The herpesvirus-based vaccine of the present invention will induce an anti-vector immune response. Where the vector is based on or highly similar to the target infectious pathogen, this anti-vector immune response may be directly relevant to protection against the infectious pathogen.

Where the target infectious pathogen is dissimilar to the herpesvirus vector (for example where the infectious pathogen is a different type of virus, or even a non-viral pathogen) the non-adaptive portion of the anti-vector immune response may still be useful for pathogen clearance.

Modification of Established Vaccines

The virus vaccine may be based on an established live vaccine already proposed or in use in the treatment and/or prevention of a disease.

Established live vaccines include the MMR vaccine which is a mixture of three live attenuated viruses, for immunization against measles, mumps and rubella.

Established vaccines for the treatment of herpes virus infections include Varivax™, a live-varicella virus vaccine against chicken pox and vaccination with live attenuated strains of MDV against MD. A live herpesvirus vaccine has also been used with some success against equine herpesvirus infections (Patel et al., (2003) Vet. Microbiology 20; 92(1-2): 1-17).

MD Vaccines

In the 1970's MD control was achieved predominantly by vaccination with herpesvirus of turkey (HVT, serotype 3). This was to some extent supplanted with the development of serotype 2 vaccines in the 1980s, such as SB-1 and 301B/1.

More recently, serotype 1 vaccines have been developed such as attenuated HPRS-16 and CVI988 (Rispens vaccine) strains. Rispens vaccine, produced from a natural isolate of low oncogenicity, has been widely used, in particular because it has been found to be highly effective against very virulent strains of the MDV virus.

For the purposes of the present invention, vaccines based on the original HVT vaccine have some advantages. For example, unlike serotype 1 and 2 strains, HVT can be produced in a cell free system. Also, as the HVT genome shows a relatively low degree of sequence identity with the MDV genome (about 70%), there is a good chance that an miRNA sequence targeting a site on the MDV genome will not significantly affect replication of an HVT-based virus vaccine.

On the other hand, serotype 1 strains, such as the Rispens vaccine induce a more effective immune response, particularly against MDV strains of high virulence. An anti-MD virus of the present invention based on an established MD vaccine has the advantage that it combines induction of an anti-MD immune response with inhibition of MDV replication via RNAi. In order to maximise the former effect, it may be desirable to use a serotype 1 vaccine.

Although serotype 1 vaccines such as Rispens have a higher degree of sequence identity to MDV than HVT, it is still possible to design a vaccine expressing an miRNA molecule that blocks replication of MD, but not the vaccine. For example, once the target sequence on an MDV gene has been selected, the corresponding sequence in the vaccine genome can be mutated to decrease the degree of identity with the MDV gene. This makes it less likely that the miRNA sequence will recognise the vaccine genome sequence. Site directed mutagenesis can be used to alter bases in any part of the vaccine genome which has a high degree of identity to the target sequence.

In order to avoid the mutations having any effect on the vaccine itself, silent mutations can be introduced which alter the DNA sequence, but do not affect the amino acid sequence of the translated protein. Such mutations are possible due to the degeneracy of the genetic code.

Disease

The modified herpesvirus vector of the present invention may be used for treating and/or preventing a disease.

'Treating' as used herein refers to treatment of a subject having a disease in order to ameliorate, cure or reduce the symptoms of the disease, or reduce or halt the progression of the disease.

The term 'preventing' is intended to refer to averting, delaying, impeding or hindering the contraction of a disease. For example, the vaccine of the present invention may be used to prevent an autoimmune disease or an allergic reaction in a subject.

The disease may be an infectious disease, such as an infectious viral disease. Infectious viral diseases of mammalians subject, such as humans include, but are not limited to, AIDS, chickenpox (varicella), common cold, dengue fever, herpes simplex, herpes roster, influenza, measles, infectious mononucleosis (glandular fever), mumps, norovirus, poliomyelitis (polio), rabies, rubella, SARS, viral encephalitis, viral gastroenteritis, viral meningitis, viral pneumonia, west Nile disease and yellow fever.

Infectious diseases of avian subject, such as chickens include, but are not limited to: avian influenza, infectious bursal disease, chicken anaemia, Newcastle disease, infectious bronchitis, Reovirus infection, infectious laryngeotracheitis, fowl pox.

In particular, the disease may be caused by a herpesvirus.

The family Herpesviridae include eight distinct viruses known to cause disease in humans, as shown in the following table:

| Human Herpesvirus (HHV) classification | | | |
|---|---|---|---|
| Type | Synonym | Subfamily | Pathophysiology |
| HHV-1 | Herpes simplex virus-1 (HSV-1) | α (Alpha) | Oral and/or genital herpes (predominantly orofacial) |
| HHV-2 | Herpes simplex virus-2 (HSV-2) | α | Oral and/or genital herpes (predominantly genital) |
| HHV-3 | Varicella zoster virus (VZV) | α | Chickenpox and shingles |
| HHV-4 | Epstein-Barr virus (EBV), lymphocryptovirus | γ (Gamma) | Infectious mononucleosis, Burkitt's lymphoma, CNS lymphoma in AIDS patients, post-transplant lymphoproliferative |

-continued

Human Herpesvirus (HHV) classification

| Type | Synonym | Subfamily | Pathophysiology |
|---|---|---|---|
| HHV-5 | Cytomegalovirus (CMV) | β (Beta) | syndrome (PTLD), nasopharyngeal carcinoma Infectious mononucleosis-like syndrome,[5] retinitis, etc. |
| HHV-6, -7 | Roseolovirus | β | Sixth disease (roseola infantum or exanthem subitum) |
| HHV-8 | Kaposi's sarcoma-associated herpesvirus (KSHV), a type of rhadinovirus | γ | Kaposi's sarcoma, primary effusion lymphoma, some types of multicentric Castleman's disease |

In animal virology the most important herpesviruses can be summarised as follows:
Subfamily Alphaherpesvirinae
  Genus Simplexvirus
    Bovine herpesvirus 2 causes bovine mammillitis and pseudo-lumpyskin disease.
    Cercopithecine herpesvirus 1, also known as Herpes B virus, causes a Herpes simplex-like disease in Macaques.
    Ateline herpesvirus 1, Spider monkey herpesvirus.
  Genus *Varicellovirus*
    Bovine herpesvirus 1 causes infectious bovine rhinotracheitis, vaginitis, balanoposthitis, and abortion in cattle.
    Bovine herpesvirus 5 causes encephalitis in cattle.
    Caprine herpesvirus 1 causes conjunctivitis and respiratory disease in goats.
    Porcine herpesvirus 1 causes pseudorabies.
    Equine herpesvirus 1 causes abortion in horses.
    Equine herpesvirus 3 causes coital exanthema in horses.
    Equine herpesvirus 4 causes rhinopneumonitis in horses.
    Canine herpesvirus 1 causes a severe hemorrhagic disease in puppies.
    Feline herpesvirus 1 causes feline viral rhinotracheitis and keratitis in cats.
    Duck herpesvirus 1 causes duck plague.
  Genus *Mardivirus*
    Gallid herpesvirus 2 causes Marek's disease.
    Gallid herpesvirus 3 (GaHV-3 or MDV-2)
    Herpesvirus of turkeys (HVT)
  Genus Ilovirus
    Gallid herpesvirus 1 causes infectious laryngotracheitis in birds.
Subfamily Betaherpesvirinae
    Porcine herpesvirus 2 causes inclusion body rhinitis in swine.
Subfamily Gammaherpesvirinae
  Genus Rhadinovirus
    Alcelaphine herpesvirus 1 causes bovine malignant catarrhal fever.
    Bovine herpesvirus 4
    Equine herpesvirus 2 causes equine cytomegalovirus infection.
    Equine herpesvirus 5

Alternatively, the disease may be an allergy, autoimmune disease, neurological disorder, hypertension or cancer.

A list of potential herpervirus miRNA-based applications is given in Table 2.

TABLE 2

| Categories | | Diseases/conditions | Potential delivery method | References |
|---|---|---|---|---|
| Infectious diseases | Animals | Bovine respiratory syncytial virus (BRSV) | Modified miRNA in BHV-1 | |
| | | Chicken anaemia virus (CAV) | Modified miRNA in MDV-1 | |
| | | Avian Influenza (AI) | Modified miRNA in ILTV | |
| | Human | Measles, Mumps, Rubella | Modified miRNA in VZV | Vaccine (2007) 25, 8741-8755 |
| | | HIV | Modified miRNA in VZV | Nature Biotech (2007) 25, 1435-43 |
| Allergy | | RNAi against CD40 | Modified miRNA of lymphotropic herpesviruses | J Immunol. 180: 8461-8469 |
| Neurological Disorders | | SCA1 mouse model- Ataxin shRNA | Modified miRNA in HSV-1 | Nature Medicine 10: 816-820 |
| | | Huntington's disease -Huntingtin ShRNA | Modified miRNA in HSV-1 | PNAS (2007) 104: 17204-9 |
| | | Alzheimer's disease transgenic mouse model- shRNA | Modified miRNA in HSV-1 | Neurosci. Let. (2008) 430, 81-86 |
| Hypertension | | RNAi against mineral corticoid receptor | Modified miRNA of different herpesviruses | Physiol Heart Circ Physiol. (2008) 294, 1880-7 |
| Autoimmunity | | CTLA linked autoimmunity mouse model | Modified miRNA of lymphotropic herpesviruses | PNAS (2006) 103: 16400-405 |
| Cancer | | Mouse xenograft Fibrosarcoma models VEGF shRNA | MHV-68/MCMV miRNA | Cancer Sci (2006) 97, 689-696 |
| | | Mouse model of metastatic Ewing's sarcoma | MHV-68/MCMV miRNA | Cancer Res (2005) 8984-8992 |
| | | Silencing oncogenic fusion genes in lymphomas | MHV-68/MCMV miRNA | Sem. Cancer Biol. (2003) 13, 283-92 |

Subject

The subject may be a mammalian subject, such as a human.

Alternatively the subject may be an avian subject, such as a poultry subject, in particular a chicken.

The technology may also be used in model animals, such as mouse models of a disease.

Administration

The choice of delivery system may depend of the number and type of subjects to be treated. The method and pharmaceutical composition of the invention may be used to treat a human or animal subject. Typically, a physician will determine the actual dosage which will be most suitable for an individual subject and it will vary with the age, weight and response of the particular subject.

Mammalian Subjects

The routes for administration (delivery) in mammalian subjects may include, but are not limited to, one or more of oral (e.g. as a tablet, capsule, or as an ingestable solution), topical, mucosal (e.g. as a nasal spray or aerosol for inhalation), nasal, parenteral (e.g. by an injectable form), gastrointestinal, intraspinal, intraperitoneal, intramuscular, intravenous, intrauterine, intraocular, intradermal, intracranial, intratracheal, intratumoural, intravaginal, intracerebroventricular, intracerebral, subcutaneous, ophthalmic (including intravitreal or intracameral), transdermal, rectal, buccal, vaginal, epidural, sublingual or systemic.

The composition administered may optionally comprise a pharmaceutically acceptable carrier, diluent, excipient or adjuvant. The choice of pharmaceutical carrier, excipient or diluent can be selected with regard to the intended route of administration and standard pharmaceutical practice. The pharmaceutical compositions may comprise as (or in addition to) the carrier, excipient or diluent, any suitable binder(s), lubricant(s), suspending agent(s), coating agent(s), solubilising agent(s), and other carrier agents known in the art.

Vaccines are conventionally administered to mammalian subjects parenterally, by injection, for example, either subcutaneously or intramuscularly.

For parenteral administration, the compositions are best used in the form of a sterile aqueous solution which may contain other agents, for example enough salts or monosaccharides to make the solution isotonic with blood.

Avian Subjects

For large numbers of birds, individual administration systems may not by practicable, so application by spray, or via feed or drinking water may be more appropriate.

For smaller numbers of birds, it may be possible to treat each bird individually, which usually results in a more uniform dosage. Individual administration methods include eye drop administration, intranasal administration and parenteral delivery.

There may be different composition/formulation requirements dependent on the different delivery systems. By way of example, the composition of the present invention may be formulated to be delivered by an oral route (e.g. in drinking water or feed, or by spray application) by a mucosal route, or parenterally in which the composition is formulated by an injectable form, for delivery, by, for example, an intravenous, intramuscular or subcutaneous route.

The composition may be formulated for in ovo or post-hatch delivery.

The term "in ovo", means into a bird egg containing a live, developing embryo.

The term "administering in ovo" or "in ovo administration", means administering the vaccine to a bird egg containing a live, developing embryo by any means of penetrating the shell of the egg and introducing the vaccine. Such means of administration include, but are not limited to, injection of the vaccine.

Various in ovo administration method are known in the art. An injection method may include the steps of making a hole is made in the egg shell at the large end of the egg using an appropriate needle to expose the egg's air cell, inserting a needle connected to a syringe through the hole and through the membrane of the air cell. and then injecting the vaccine into the egg. The site of injection can be within any region of the egg or embryo. Preferably, injection is done axially through the centre of the large end of the egg into the amnion.

An automated egg injection system can be used. Such systems known in the art (see for example U.S. Pat. Nos. 4,681,063, 4,040,388, 4,469,047, and 4,593,646).

Post-hatch vaccination systems for birds include spray applications and administration via feed or drinking water.

For spray applications a special cabinet may be used. Chicks can be vaccinated in the hatchery because the sprayer enables uniform distribution. A certain amount of spray (such as 20 ml) is delivered for each box of 100 chicks. Chicks "preen" to clean and dry their feathers and ingest the vaccine. Red dye mixed in with the vaccine gets their attention and stimulates preening, and also indicates which boxes of chicks have been vaccinated.

Administration via feed/drinking water is less uniform that spraying due to differences in uptake between birds. There is also a possible contamination problem. However, this type of administration is possible for older birds (i.e. when hatchery application is not possible).

Where the composition is to be delivered mucosally through the gastrointestinal mucosa, it should be able to remain stable during transit though the gastrointestinal tract; for example, it should be resistant to proteolytic degradation, stable at acid pH and resistant to the detergent effects of bile.

Method

In a second aspect, the present invention provides a method for producing a vector according to the first aspect of the invention, which comprises the step of introducing one or more mutations in the genomic miRNA encoding sequence of a herpesvirus.

In order that the pri-miRNA forms a stem-loop structure, symmetrical mutations may be made in the sequences encoding the strands forming the stems of the stem-loop structure.

The mutation may be an addition, substitution or deletion. Single i.e. point mutations may be made, for example by site-directed mutagenesis. If, on the other hand, multiple mutations would need to be made in order to arrive at the desired sequence, it may be simpler to excise and ligate in a foreign sequence.

The term “foreign” indicates a miRNA-encoding sequence which is different from the endogenous sequence, and which produces a different, heterologous, miRNA.

The foreign sequences substituted in for each strand-encoding sequence may include deliberate mismatches so that the modified pre-miRNA mimics the structural features of the natural pre-miRNA.

In one embodiment the method of the invention involves the following:

(i) amplification of the miRNA sequence of a herpesvirus;

(ii) mutation of the miRNA;

(iii) generation of a mutant herpesvirus vector which comprises a genomic sequence encoding the modified miRNA.

Mutant clones may be generated by methods known in the art, such as BAC mutagenesis.

Figure 4A:
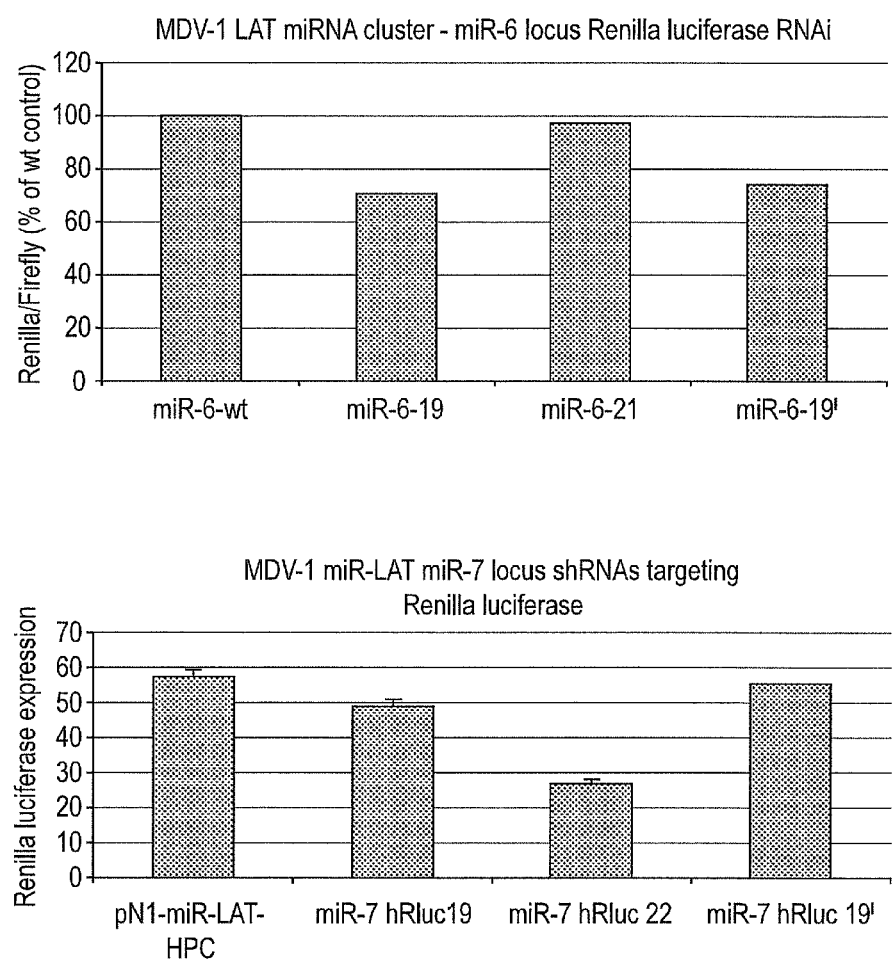
FIG. 4A shows silencing of a luciferase reporter gene using MDV miR-6 and miR-7 loci shRNA.
Figure 5:
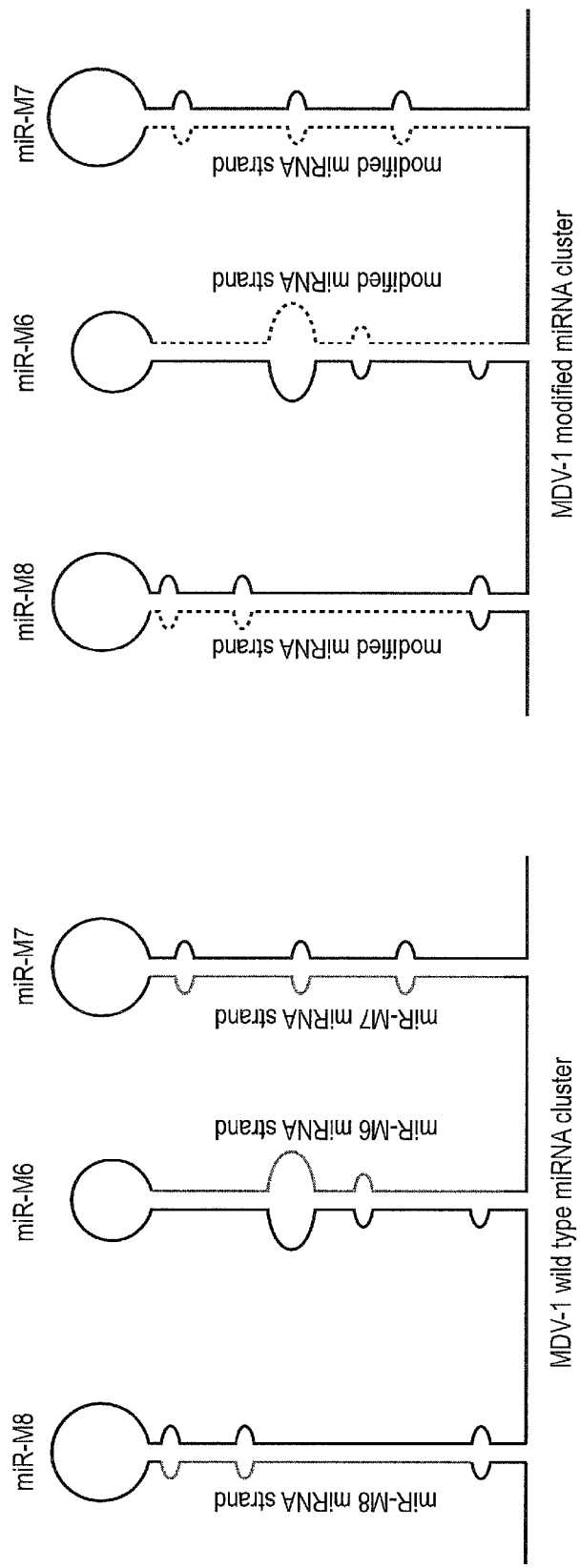
FIG. 5 is a diagrammatic representation of the structure of modified miRNAs in the modified MDV-1 miRNA cluster, in which miR-M8, miR-M6 and miR-M7 have been modified.

The invention will now be further described by way of Examples, which are meant to serve to assist one of ordinary skill in the art in carrying out the invention and are not intended in any way to limit the scope of the invention.

miR-7-hRluc-22 and miR6-hRluc19 constructs are functional in silencing the luciferase reporter gene (FIG. 4A).

Methods

Constructs for the Luciferase Assays with Luciferase Shrna at the Mir-7 Locus

The synthetic miR-LAT sequence featured two BsmBI restriction sites, each on opposite strands of the DNA, to permit the insertion of annealed DNA oligonucleotides for the replacement of miR-6. For replacement of miR-7, two AarI restriction sites, also on opposing strands of the DNA, were utilised for the insertion of annealed DNA oligonucleotides. The shRNAs constructs are cloned into pEGFP vector to drive the expression from the pCMV promoter.

Briefly, the miR-LAT-HPC vector was digested with AarI, gel purified and used in a ligation reaction with the annealed complimentary DNA oligonucleotides encoding the *Renilla* luciferase shRNAs (see below). All recombinant plasmids were DNA sequenced to verify the luciferase inserts.

```
                                                              (SEQ ID NO: 1)
pN1-miR-LAT-HPC miR-7 locus
                         BamHI  AarI
AACGCTCCAAG|GAGA ACTGGCAGGTGCGGATCCGCACCTGCAGTT|TTTG GGGGA TTGCGAGGTTC CTCT|TGACCGTCCACGCCTAGGCGTGGACGTCAA AAAC|CCCCT
                                              AarI Oligonucleotides for the generation of luciferase shRNA
                                                              (SEQ ID NO: 2)
5'-GAGAAC GTTGATGAAGGAGTCCAGCTCG TCTCTCCTACCAGCAAC CGAACTGGACTACTTCATGAAC GTT-3'
                                                              (SEQ ID NO: 3)
5'-CAAAAC GTTCATGAAGTAGTCCAGTTCG GTTGCTGGTAGGAGAGA CGAGCTGGACTCCTTCATCAAC GT-3'
Note:
underlined sequences in the oligonucleotides represent overhangs required
for insertion into the AarI site.
```

EXAMPLES

Example 1

Modification of the MDV1-miR-M8-13-6-7-10 Cluster

Figure 2:
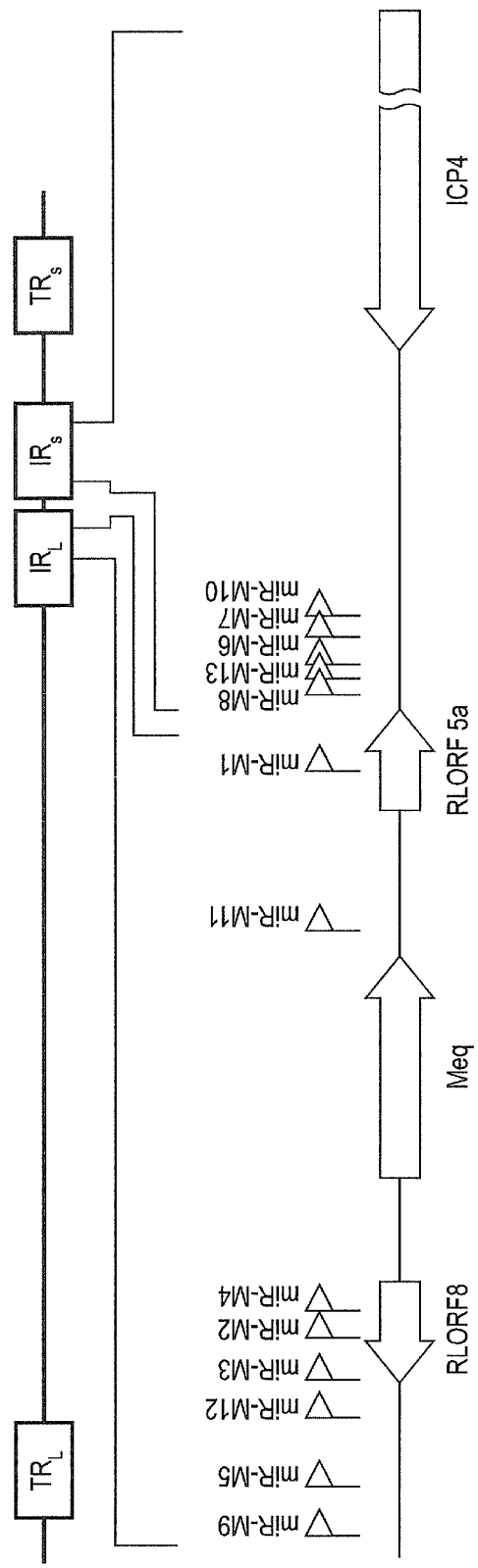
FIG. 2 shows the genomic locations of MDV-1 miRNAs. The schematic diagram shows where the MDV-1 miRNAs (small arrowheads) identified in this report map. The $TR_L$ and $IR_L$ regions flanking the unique long region and the $TR_S$ and $IR_S$ regions flanking the unique short regions are shown. Genomic positions and orientations of MDV ORFs contained in the miRNA loci are indicated.

Marek's disease virus type 1 (MDV-1) encodes thirteen miRNAs clustered in the MEQ and LAT regions of the viral genome (Yao et al (2008) J. Virol 82:4007-4015). The predicted secondary structures of all thirteen MDV pre-miRNAs are shown in FIG. 1. The genomic location of each miRNA is given in FIG. 2. These include the MDV1-miR-M8-13-6-7-10 cluster located between the 'a-like' sequence and the ICP4 within the large intron of the LAT. Of the five miRNAs encoded from this cluster, miR-M13 and miR-M10 are expressed at very low levels. The complete sequence of the cluster with the miRNA sequences are shown in FIG. 3.

The cluster region is amplified by PCR and cloned into a vector to facilitate manipulation. The MDV-1 miR-M7 microRNA was mutated to modify it into a luciferase siRNA as shown in FIG. 4. Similar mutagenesis was also carried out for miR-M6.

Example 2

Silencing of a Reporter Gene

Mutant clones of MDV were generated by BAC mutagenesis and the silencing effect of the modified miRNAs on expression of Luciferase was tested. A similar procedure was repeated independently for miR-M6. Preliminary results using this modified miR-M7 and miR-M6 have shown that DNA Transfections and Luciferase Assays Line 0 chicken embryo fibroblast (CEF)-derived DF-1 cell line was grown in DMEM medium supplemented with 10% fetal calf serum (FCS) and 1% sodium puruvate. Transfection into DF-1 cells for luciferase reporter assays was carried out in 24-well plates with Lipofectamine 2000 (Invitrogen) according to the manufacture's protocols. Briefly, 24-well plates were seeded ($1.1 \times 10^5$ cells/well) 24 hours before transfection, and 500 ng of shRNA expression constructs (and mutant control vectors) were co-transfected with 500 ng psiCHECK™-2 vectors (Promega). Firefly and *Renilla* luciferase activities were measured consecutively with the Dual-Luciferase® Reporter Assay System (Promega) using the Lucy 1 luminometer (Anthos Labtec). In all cases, a constitutively expressed Firefly luciferase activity in psiCHECK™-2 vector served as a normalisation control for transfection efficiency.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in cellular studies using flow cytometry or related fields are intended to be within the scope of the following claims.

The invention claimed is:

1. A herpesvirus vector comprising a modified endogenous microRNA (miRNA) cluster, wherein the endogenous miRNA cluster is modified such that the vector encodes a miRNA against a target sequence in a gene which is different from the gene silenced by the unmodified miRNA.

2. A herpesvirus vector according to claim 1, wherein the miRNA is against a target sequence from a host gene.

3. A herpesvirus vector according to claim 1, wherein the miRNA is against a target sequence from an infectious pathogen.

4. A herpesvirus vector according to claim 3, wherein the infectious pathogen is a virus.

5. A herpesvirus vector according to claim 4, wherein the infectious pathogen is a herpesvirus.

6. A herpesvirus vector according to claim 5, which is based on a pathogenic herpesvirus.

7. A herpesvirus vector according to claim 6, which comprises a modified genomic sequence that encodes a miRNA against a target sequence from the pathogenic herpesvirus on which the vector is based.

8. A herpesvirus vector according to claim 7, wherein the target sequence encoding portion of the vector genome is modified, such that it is not itself silenced by the miRNA.

9. A herpesvirus vector according to claim 1 which is based on a Marek's disease virus.

10. A herpesvirus vector according to claim 1, which comprises a genomic sequence modified to express a plurality of modified miRNAs.

* * * * *

UNITED STATES PATENT AND TRADEMARK OFFICE
CERTIFICATE OF CORRECTION

PATENT NO. : 8,501,466 B2
APPLICATION NO. : 12/997844
DATED : August 6, 2013
INVENTOR(S) : Nair et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 74 days.

Signed and Sealed this
Fifteenth Day of September, 2015

Michelle K. Lee
*Director of the United States Patent and Trademark Office*

SEQUENCE LISTING

<160> NUMBER OF SEQ ID NOS: 32

<210> SEQ ID NO 1
<211> LENGTH: 54
<212> TYPE: DNA
<213> ORGANISM: Artificial Sequence
<220> FEATURE:
<223> OTHER INFORMATION: pN1-miR-LAT-HPC miR-7 locus

<400> SEQUENCE: 1
aacgctccaa ggagaactgg caggtgcgga tccgcacctg cagttttttgg ggga      54

<210> SEQ ID NO 2
<211> LENGTH: 70
<212> TYPE: DNA
<213> ORGANISM: Artificial Sequence
<220> FEATURE:
<223> OTHER INFORMATION: Oligonucleotide

<400> SEQUENCE: 2
gagaacgttg atgaaggagt ccagctcgtc tctcctacca gcaaccgaac tggactactt      60
catgaacgtt      70

<210> SEQ ID NO 3
<211> LENGTH: 70
<212> TYPE: DNA
<213> ORGANISM: Artificial Sequence
<220> FEATURE:
<223> OTHER INFORMATION: Oligonucleotide

<400> SEQUENCE: 3
caaaaacgtt catgaagtag tccagttcgg ttgctggtag gagagacgag ctggactcct      60
tcatcaacgt      70

<210> SEQ ID NO 4
<211> LENGTH: 71
<212> TYPE: RNA
<213> ORGANISM: Marek's disease virus type 1 (MDV-1)

<400> SEQUENCE: 4
ccuuuugcuu guucacugug cggcauuauu acauuuacac cggguaaugc ugcgcaugaa 60
agagcgaacg g 71

<210> SEQ ID NO 5
<211> LENGTH: 71
<212> TYPE: RNA
<213> ORGANISM: Marek's disease virus type 1 (MDV-1)

<400> SEQUENCE: 5
aagaaaguug uauucugccc gguaguccgu uuguaagguc uuggaacgga cugccgcaga 60
auagcuuucu u 71

<210> SEQ ID NO 6
<211> LENGTH: 66
<212> TYPE: RNA
<213> ORGANISM: Marek's disease virus type 1 (MDV-1)

<400> SEQUENCE: 6
ggcaugaaaa ugugaaaccu cucccgcuag aaauagaauc ugcugggggg uucacauuuu 60
uaaguu 66

```
<210> SEQ ID NO 7
<211> LENGTH: 68
<212> TYPE: RNA
<213> ORGANISM: Marek's disease virus type 1 (MDV-1)

<400> SEQUENCE: 7
gaaguuuaau gcuguaucgg aacccuucgu ucggugacca cgaaugguuc ugacagcaug     60
acccuuuc                                                             68

<210> SEQ ID NO 8
<211> LENGTH: 69
<212> TYPE: RNA
<213> ORGANISM: Marek's disease virus type 1 (MDV-1)

<400> SEQUENCE: 8
ugaaccguau gcgaucacau ugacacgguu uaaaauacau acguguguau cguggucguc     60
uacuguuug                                                            69

<210> SEQ ID NO 9
<211> LENGTH: 66
<212> TYPE: RNA
<213> ORGANISM: Marek's disease virus type 1 (MDV-1)

<400> SEQUENCE: 9
gaaaaucugu uguuccguag uguucucgug acacuaacuc gagaucccug cgaaaugaca     60
guuuuc                                                               66

<210> SEQ ID NO 10
<211> LENGTH: 67
<212> TYPE: RNA
<213> ORGANISM: Marek's disease virus type 1 (MDV-1)

<400> SEQUENCE: 10
aacuguuauc ucggggagau cccgaucucu ccuaccagca acucgagauc ucuacgagau     60
uacaguu                                                              67

<210> SEQ ID NO 11
<211> LENGTH: 72
<212> TYPE: RNA
<213> ORGANISM: Marek's disease virus type 1 (MDV-1)

<400> SEQUENCE: 11
aaaccuauug uucguggguu gguuucgauc uaucguucuc guacugcgug accucuacgg     60
aacaauaguu uu                                                        72

<210> SEQ ID NO 12
<211> LENGTH: 70
<212> TYPE: RNA
<213> ORGANISM: Marek's disease virus type 1 (MDV-1)

<400> SEQUENCE: 12
gcgguuuuuc uccuuccccc cggaguucac uguaucguac guuguaaacu ccgagggcag     60
gaaaaagugc                                                           70

<210> SEQ ID NO 13
<211> LENGTH: 68
<212> TYPE: RNA
<213> ORGANISM: Marek's disease virus type 1 (MDV-1)

<400> SEQUENCE: 13
```
uggcguuguc ucguagaggu ccagaucucu ccuguugcaa cucgaaaucu cuacgagaua    60
acaguuug                                                             68

<210> SEQ ID NO 14
<211> LENGTH: 65
<212> TYPE: RNA
<213> ORGANISM: Marek's disease virus type 1 (MDV-1)

<400> SEQUENCE: 14
aaauuuuccu uaccguguag cuuagacucg aagaacuauu uuugaguuac auggucaggg    60
gauuu                                                                65

<210> SEQ ID NO 15
<211> LENGTH: 62
<212> TYPE: RNA
<213> ORGANISM: Marek's disease virus type 1 (MDV-1)

<400> SEQUENCE: 15
gaucaaggcc cuccguauaa uguaaauguc caaagguuug cauaauacgg agggucuga     60 uc                                                                   62

<210> SEQ ID NO 16
<211> LENGTH: 61
<212> TYPE: RNA
<213> ORGANISM: Marek's disease virus type 1 (MDV-1)

<400> SEQUENCE: 16
aguuuuccag gagauuuccc gguuucgacu gccgaagcau ggaaacgucc ugggaaaauc    60
u                                                                    61

<210> SEQ ID NO 17
<211> LENGTH: 969
<212> TYPE: DNA
<213> ORGANISM: Marek's disease virus type 1 (MDV-1)

<400> SEQUENCE: 17
gcggagttat atgttacgcg gttcccagcc tataagaatc gtggtgttgg cgccaaaaaa    60
tgcgcgccaa caaaaaggcg ccaaaaaatt gcgcgccatt gtttggcgcc ttttctgcg   120 ccgttttcaa aatcgcgcca taccaatttc aaagttcccg ccatttggcc aacacgctat   180
tatccctgca tgatcttctt taattggacg acattcctcg attcccgatc cacatatcca   240
gtgacaggag ttcggaataa acgttgtgat acgcgatcga gttttcgtgg catattccta   300
cggaaaccta tgttctgtg gttggttttcg atctatcgtt ctcgtactgc gtgacctcta   360
cggaacaata gttttccagg agatttcccg gtttcgactg ccgaagcatg gaaacgtcct   420
gggaaaatct gttgttccgt agtgttctcg tgacactaac tcgagatccc tgcgaaatga   480
cagttttctc tgggaattac atcgtcctga ttgtcgcgac atggaatgga agcctcatag   540
gaagaactcg atgtgatgat gctctctagc aagagagcc gcgaacgctc caaggagaac   600
tgttatctcg gggagatccc gatctctcct accagcaact cgagatctct acgagattac   660 agttttggg ggaaatgtgt cctcagaact gcttaatcgt agaagcttcc tagtggatgg   720
cgttgtctcg tagaggtcca gatctctcct gttggcaact cgaaatctct acgagataac   780
agtttgtcta ggaaactttc ctcccaacta agagcgatg acttaggaag taaacgtgcc   840
ctcatcaccg cccttacaca ctgctagtca ttcatgtaca ttgcgattgt gccttggtgc   900
ggggcggttc ctaggcacca tttatcttgt attcctgtac atcccctcct taatacttta   960

-continued attggagcc                                                                969

<210> SEQ ID NO 18
<211> LENGTH: 27
<212> TYPE: DNA
<213> ORGANISM: Artificial Sequence
<220> FEATURE:
<223> OTHER INFORMATION: siRNA sequence

<400> SEQUENCE: 18
acgtgcugga cuccuucauc aacuacu                                            27

<210> SEQ ID NO 19
<211> LENGTH: 90
<212> TYPE: DNA
<213> ORGANISM: Marek's disease virus type 1 (MDV-1)

<400> SEQUENCE: 19
aacgctccaa ggagaactgt tatctcgggg agatcccgat ctctcctacc agcaactcga        60
gatctctacg agattacagt ttttggggga                                         90

<210> SEQ ID NO 20
<211> LENGTH: 37
<212> TYPE: RNA
<213> ORGANISM: Artificial Sequence
<220> FEATURE:
<223> OTHER INFORMATION: miR-7-hRluc-19

<400> SEQUENCE: 20
gagaacguug augaaggagu ccagccgauc ucuccua                                 37

<210> SEQ ID NO 21
<211> LENGTH: 36
<212> TYPE: RNA
<213> ORGANISM: Artificial Sequence
<220> FEATURE:
<223> OTHER INFORMATION: miR-7-hRluc-19

<400> SEQUENCE: 21
ccagcaacuc gacuggacua cuucaugaac guuuuu                                  36

<210> SEQ ID NO 22
<211> LENGTH: 70
<212> TYPE: DNA
<213> ORGANISM: Artificial Sequence
<220> FEATURE:
<223> OTHER INFORMATION: miR-7-hRluc-19-t

<400> SEQUENCE: 22
gagaacgttg atgaaggagt ccagccgatc tctcctacca gcaactcgac tggactactt        60
catgaacgtt                                                               70

<210> SEQ ID NO 23
<211> LENGTH: 70
<212> TYPE: DNA
<213> ORGANISM: Artificial Sequence
<220> FEATURE:
<223> OTHER INFORMATION: miR-7-hRluc-19-b

<400> SEQUENCE: 23
caaaaacgtt catgaagtag tccagtcgag ttgctggtag gagagatcgg ctggactcct        60
tcatcaacgt                                                               70

<210> SEQ ID NO 24

```
<211> LENGTH: 37
<212> TYPE: RNA
<213> ORGANISM: Artificial Sequence
<220> FEATURE:
<223> OTHER INFORMATION: miR-7-hRluc-22

<400> SEQUENCE: 24
gagaacguug augaaggagu ccagcucguc ucuccua                              37

<210> SEQ ID NO 25
<211> LENGTH: 36
<212> TYPE: RNA
<213> ORGANISM: Artificial Sequence
<220> FEATURE:
<223> OTHER INFORMATION: miR-7-hRluc-22

<400> SEQUENCE: 25
ccagcaaccg aacuggacua cuucaugaac guuuuu                               36

<210> SEQ ID NO 26
<211> LENGTH: 70
<212> TYPE: DNA
<213> ORGANISM: Artificial Sequence
<220> FEATURE:
<223> OTHER INFORMATION: miR-7-hRluc-22-t

<400> SEQUENCE: 26
gagaacgttg atgaaggagt ccagctcgtc tctcctacca vcaaccgaac tggactactt    60
catgaacgtt                                                            70

<210> SEQ ID NO 27
<211> LENGTH: 70
<212> TYPE: DNA
<213> ORGANISM: Artificial Sequence
<220> FEATURE:
<223> OTHER INFORMATION: miR-7-hRluc-22-b

<400> SEQUENCE: 27
caaaaacgtt catgaagtag tccagttcgg ttgctggtag gagagacgag ctggactcct    60
tcatcaacgt                                                            70

<210> SEQ ID NO 28
<211> LENGTH: 36
<212> TYPE: RNA
<213> ORGANISM: Artificial Sequence
<220> FEATURE:
<223> OTHER INFORMATION: miR-7-hRluc-19'

<400> SEQUENCE: 28
gagaacugug uugaugaagg aguccagcuc ucuccu                               36

<210> SEQ ID NO 29
<211> LENGTH: 36
<212> TYPE: RNA
<213> ORGANISM: Artificial Sequence
<220> FEATURE:
<223> OTHER INFORMATION: miR-7-hRluc-19'

<400> SEQUENCE: 29
ccagcaacgc uagacuccug caucaagaca guuuuu                               36

<210> SEQ ID NO 30
<211> LENGTH: 70
<212> TYPE: DNA
<213> ORGANISM: Artificial Sequence
<220> FEATURE:
```

```
<223> OTHER INFORMATION: miR-7-hRluc-19' -t

<400> SEQUENCE: 30
gagaactgtg ttgatgaagg agtccagctc tctcctacca gcaacgctag actcctgcat    60
caagacagtt                                                          70

<210> SEQ ID NO 31
<211> LENGTH: 70
<212> TYPE: DNA
<213> ORGANISM: Artificial Sequence
<220> FEATURE:
<223> OTHER INFORMATION: miR-7-hRluc-19' -b

<400> SEQUENCE: 31
caaaaactgt cttgatgcag gagtctagcg ttgctggtag gagagagctg gactccttca    60
tcaacacagt                                                          70

<210> SEQ ID NO 32
<211> LENGTH: 27
<212> TYPE: DNA
<213> ORGANISM: Artificial Sequence
<220> FEATURE:
<223> OTHER INFORMATION: siRNA sequence

<400> SEQUENCE: 32
aguaguugau gaaggagucc agctcgt                                       27
```